(12) United States Patent
Blundy et al.

(10) Patent No.: US 6,294,713 B1
(45) Date of Patent: Sep. 25, 2001

(54) MODIFICATION OF SUCROSE ACCUMULATION IN THE TUBERS OF POTATOES

(75) Inventors: Keith Stuart Blundy, Histon; Michael Meyrick Burrell, Cottenham; George Stephen Morris; Christopher John Robert Thomas, both of Cambridge, all of (GB)

(73) Assignee: Advanced Technologies (Cambridge) Limited, London (GB)

( * ) Notice: Subject to any disclaimer, the term of this patent is extended or adjusted under 35 U.S.C. 154(b) by 0 days.

(21) Appl. No.: 07/925,978

(22) Filed: Aug. 5, 1992

(30) Foreign Application Priority Data

Aug. 8, 1991 (GB) .................................................. 9117159

(51) Int. Cl.[7] ............................. C12N 15/82; C12P 19/04; A01H 5/00; A01H 5/06; A01H 5/10
(52) U.S. Cl. ......................... 800/284; 800/286; 800/287; 800/317.2
(58) Field of Search .......................... 536/27; 435/172.1, 435/240.51; 800/205, 255, DIG. 42, 284, 286, 287, 317.2; 935/9, 35, 67

(56) References Cited

FOREIGN PATENT DOCUMENTS

0438904 A1    7/1991   (EP) .
WO 92/01782   2/1992   (WO) .
WO 92/16631   10/1992  (WO) .

OTHER PUBLICATIONS

RN Trethewey et al (1999) Planta 208:227–338.*
RB Flavell (1994) Proc Natl Acad Sci USA 91: 3490–3496.*
J l Medford et al. (1989) Plant Cell 1:403–413.*
T Takahashi (1991) Gen Bank Accession No. D00710.*
L H Bailey (1943) The Standard Cyclopedia of Horticulture vol. III pp. 2767–2771.*
D T Well et al (198) Plant Molecular Biology 9:365–375.*
J L Walker et al. (1989) Plant Physiology 89:518–524.*
M Jaye et al. (1983) Nucleic Acids Research 11:2325–2335.*
R H Aebersold et al. (1987) Proc Natl Acad Sci USA 84:6970–6974.*
S J Rothstein et al (1987) Proc Natl Acad Sci USA 84:8439–8443.*
A R van der Krol et al. (1990) Plant Cell 2: 291–299.*
J. Cell Biochem. Suppl. vol. 15A.

* cited by examiner

Primary Examiner—David T. Fox
(74) Attorney, Agent, or Firm—Pennie & Edmonds LLP

(57) ABSTRACT

A sequence from the gene encoding for reduced sugar production is used, in sense or antisense orientation to transform potato such that less sugar is stored in the tubers of the transformed plant.

8 Claims, 1 Drawing Sheet

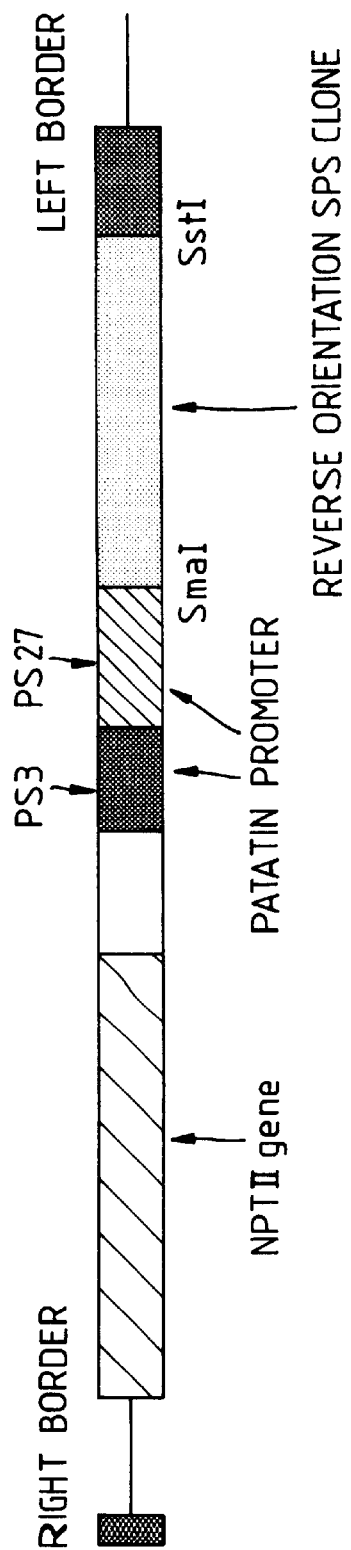

SEQUENCE LISTING (1) GENERAL INFORMATION:

(iii) NUMBER OF SEQUENCES:  1

(2) INFORMATION FOR SEQ ID NO: 1:

(i) SEQUENCE CHARACTERISTICS:
        (A) LENGTH:        444 base pairs
        (B) TYPE:          nucleic acid
        (C) STRANDEDNESS:  single
        (D) TOPOLOGY:      linear (ii) MOLECULE TYPE:        genomic DNA (iii) HYPOTHETICAL:        yes (iv) ANTI-SENSE:           yes (v) FRAGMENT TYPE:

(vi) ORIGINAL SOURCE:
        (A) ORGANISM:       Plant (potato)
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:      Plant
        (H) CELL LINE:
        (I) ORGANELLE:

(vii) IMMEDIATE SOURCE:
        (B) CLONE:

(xi) SEQUENCE DESCRIPTION: SEQ ID NO: 1:

| | | | | | |
|---|---|---|---|---|---|
| AAGCCGGAGG | AGATTACGAA | GGAGGAGTAT | GCTGCATTCT | ACAAGAGCCT | 50 |
| GACAAATGAT | TGGGAAGAGC | ATTTGGCTGT | CAAGCACTTC | TCTGTTGAGG | 100 |
| GTCAGCTGGA | GTTCAAGGCT | GTTCTTTTTA | TTCCAAAGAG | AGCTCCTTTT | 150 |
| GACCTCTTTG | ACACCAAGAA | GAAGCCCAAC | AATATCAAGC | TCTATGTTCG | 200 |
| CCGTGTGTTC | ATCATGGATA | ACTGCGAGGA | ATTGATTCCT | GAATATTTGA | 250 |
| GCTTTGTAAA | GGGTATTGTG | GATTCCGAGG | ACCTTCCCCT | CAACATCTCT | 300 |
| AGAGAGATGT | TACAGCAGAA | TAAGATCCTG | AAGGTTATTC | GCAAAAACTT | 350 |
| GGTAAAGAAG | TGCATTGAGC | TATTCTTTGA | AATCGCCGAA | AACAAAGAAG | 400 |
| ACTATGACAA | GTTCTATGAG | GCCTTCTCAA | AGAACCTCAA | GCTT | 444 |

MODIFICATION OF SUCROSE ACCUMULATION IN THE TUBERS OF POTATOES

BACKGROUND OF THE INVENTION

1. Field of the Invention

The subject invention relates to a process of reducing the accumulation of sugar in the tubers of potato plants.

2. Brief Description of Related Art

It is an object of the invention to effect a reduction in the amount of sucrose and/or free sugars derived from sucrose in potato tubers and/or one or more of sucrose, glucose or fructose formed from starch in potato tubers.

It has been suggested that sucrose phosphate synthase (SPS) (EC2.3.1.14) regulates the synthesis of sucrose in the leaves of higher plants (Stitt, N., Quick, P., Physiologia Plantarum 77 633–641, 1989) and that the enzyme occurs in tissues which synthesise sucrose (Stitt, M., Kaber, S., and Kerr, P., The Biochemistry of Plants 10 327–409, 1987, Academic Press).

Sucrose accumulates in potato tubers stored at low temperatures. Such accumulation of sugars at low temperature presents a significant problem to processors of potatoes. For example, producers of crisps and chips (french fries) have found that the presence of increased sugar tends to cause undue browning of the products during the frying process.

SUMMARY OF THE INVENTION

The subject invention provides a process for the preparation of a transgenic plant, which process comprises transforming a potato cell with a chimaeric gene comprising a suitable promoter for expression in a cell of a potato tuber and a sense or antisense genomic sequence for sugar reduction and regenerating a potato plant from the transformed cell, whereby in respect of the regenerated plant, as compared to a control plant not the product of said process, less of the sucrose imported into the tuber(s) from non-tuber parts of the plant is stored as sucrose and/or free sugar in the tuber(s) and/or less of one or more of sucrose, glucose or fructose is formed from starch stored in the tuber(s). The promoter should be such as to ensure that the sequence from the gene for sucrose phosphate synthase is expressed in the non-photosynthetic storage cells of the potato tuber.

The genome from which the sense or antisense sequence is derived may be, for example, potato, but the sequence may be derived from any other organism comprising a DNA sequence for sugar reduction which is sufficiently homologous to the endogenous sequence in the target potato plant.

BRIEF DESCRIPTION OF THE DRAWING

The drawing is a diagram of a chimaeric gene used in the invention.

DETAILED DESCRIPTION OF THE INVENTION

It is a result of carrying out the invention that the synthesis of sugar may be reduced.

The procedure used to produce the chimaeric gene is illustrated by way of example.

Purification of SPS from Potato Tubers
All Procedures are Performed at 4° C. Unless Otherwise Stated.
Extraction:
10 kg of potato tubers are washed thoroughly and any damaged or diseased tubers are discarded prior to further processing. Five 2 kg batches of washed tubers are diced and juiced, using a Waring commercial juice extractor. The resultant juice is collected into loooml of 2×extraction buffer (60 mM HEPES pH7.5, 10 mM MgCl, 8 DTT, 4 EDTA, 10 mM NAF, 2 PMFS, 0.2 $\mu$M Pepstatin A and 20% glycerol (v:v) with 200 of insoluble PVP). The collected juice and buffer are continually stirred to ensure complete mixing. Approximately 2.51 of extract was obtained from 2 kg of potatoes.
PEG Precipitation:
A 50% (w:v) PEG6000 solution is used to adjust the extract to a PEG concentration of 5% (1:9 v:v PEG to extract). After stirring for 15 min the extract is centrifuged at 9000 g in a Beckman centrifuge, model J2 -21, using a JA10 rotor for 20 min. The supernatant from each 2 kg batch is retained and combined.
Q-Sepharose Anion Column:
The bulked supernatant from PEG precipitation (ca. 141 for 10 kg of tubers) is diluted by a factor of two with water then batch absorbed onto 1500 g of Q-sepharose resin (Pharmacia) for 4 -6 h. The resin is then poured into a 10×200 column. Subsequently the column is washed with 21 of 50 mM NaCl in equilibration buffer, followed by 500 mM NaCl in equilibrium buffer and then 750 mM NaCl in equilibration buffer (21 each). Finally the column is eluted with 41 of equilibration buffer containing 1 M NaCl. Fractions are collected and assayed for SPS activity and protein content.
Phenyl Sepharose Hydrophobic Column:
A 300 ml column (Pharmacia XK-50) is filled with phenyl sepharose CL4 B (Pharmacia) which has been treated with 1 1 of 6 M urea, washed with 21 distilled water and equilibrated with 21 of buffer (MOPS 30 mM pH7.00, MgCl 5 mM, DTT 2 mM, EDTA 0.5 mM). The fractions from the Q-Sepharose column (ca. 1000 ml) containing SPS activity are combined and loaded onto the column at 1 ml/min. The column is then washed with the equilibration buffer until the optical density of the eluent at 280 nm has returned to background. The SPS is then eluted from the column with equilibration buffer containing 6 M urea. Fractions (15 ml) are collected and assayed for SPS activity. SPS containing fractions are pooled, dialysed against column equilibration buffer concentrated against 50% PEG 6000 made up in the same buffer, reassayed for SPS activity and protein, and stored at −80° C. after the addition of glycerol to 20% v:v. In this state SPS activity is partially stable for up to eight months providing that repeated freeze thaw cycles are avoided.
Fructose-6 -phosphate Sepharose (Fru-6 -P) Affinity Column:
30 ml of Sepharose bound Fru-6 -P resin manufactured as described below is loaded into a Pharmacia XK26 column as a slurry. The column is then equilibrated with 20 column volumes of buffer (30 mM MOPS-NaOH pH7.0, 5 mM DTT, 10% glycerol, 5 mM isoleucine). Peak SPS activity derived from the phenyl column containing up to 100 mg of protein is loaded onto the column at 1 ml/min. To elute SPS, the column is washed with ten column volumes of buffer (30 mM MOPS-NaOH pH7.0, 5 mM DTT, 10% glycerol, 5 mM isoleucine), followed by ten column volumes of the same buffer modified by the addition of 400 mM NaCl. Finally the column is eluted with ten volumes of base buffer plus 400 mM NaCl and 100 mM Fru-6 -P. Fractions are taken throughout the elution and assayed for SPS activity and protein content. The peak activity region is identified and dialysed against buffer (30 mM MOPS-NaOH pH7.0, 5 mM DTT, 0.5 mM EDTA, 10% glycerol). SPS activity from this stage, to the end of the purification becomes progressively less stable and very susceptible to freeze thaw stress, therefore it is important to complete the purification rapidly and avoid freezing of the sample.

Mono Q Anion Column:

The dialysed SPS sample is passed through a 0.22 μm filter and up to 30 mg of protein loaded onto an HR 10/10 Mono Q column set up on an FPLC (Pharmacia). The column is prepared by washing with 50 ml of 1M NaCl in buffer (30 mM MOPS-NaOH pH7.0, 5 mM DTT, 0.5 mM EDTA, 10% glycerol), followed by 50 ml of equilibration buffer. The column is then eluted until the optical density at 280 nm returns to its baseline value. A 0-500 mM NaCl gradient is then run over 50 ml and 1 ml fractions assayed for SPS activity, active fractions combined and reassayed for SPS and protein. The sample is then concentrated against 50% PEG6000 made up in equilibration buffer before dialysing against equilibration buffer.

UDPG Agarose Affinity Column:

Up to 5 mg of Mono Q derived SPS protein is loaded onto a UDP glucuronic acid agarose column (5 ml) that has been equilibrated with 25 ml of base buffer (30 mM MOPS-NaOH pH7.0, 5 mM DTT, 0. 5 mM EDTA, 10% glycerol). After 15 min the loaded sample is displaced with buffer, collected and reloaded twice more for 15 min each time. The column is then washed with 25 ml of equilibration buffer, followed by 20 ml of equilibration buffer containing 50 mM KCl to remove weakly bound proteins. The major SPS fraction is then eluted with equilibration buffer containing 125 mM KCl followed by 50 ml of buffer containing 250 mM KCl. Fractions are collected and assayed for SPS activity and protein content.

Manufacture of Fru-6 -P Sepharose Resin:

Epoxy activated Sepharose 6 B resin (Pharmacia) is used as a medium to which Fructose-6 -phosphate could be directly coupled via its hydroxyl groups. 10 g of resin is swollen in water (to give about 30 ml swollen resin) and washed with 1000 ml of distilled water on a glass sinter. The epoxy groups are then activated by washing with 1000 ml of 0.1M sodium carbonate/bicarbonate buffer, pH9.9. Activated resin is then transferred to a sterile container with 15 ml of the bicarbonate buffer and 1 g (3.29 mmols) of Fru-6 -P. The reaction vessel is shaken for 16 h at room temperature. Following this the resin is washed in a glass sinter with 1 l of each of the following buffers, in order to remove any excess Fru-6 -P and to prepare any unreacted epoxy groups for capping with ethanolamine, 0.1M sodium carbonate/sodium hydrogen carbonate pH 9.9, water, 0.1M sodium hydrogen carbonate pH8.0 and 0.1M sodium acetate pH4.0. Estimation of the Fru-6 -P remaining in the solution should indicate that the reaction is complete in 16 h. Any unreacted groups are then capped by shaking in 15 ml of 1M ethanolamine overnight. The Fru-6 -P resin is then prepared for use by washing with 1 l of each of the following 0.1M disodium carbonate pH9.9, 0.1M sodium borate 0.5M, sodium chloride pH8.0 and 0.1M sodium acetate pH4.0. If the resin is not to be used immediately it is stored at 4° C. in the last wash solution with 0.02% (w:v) sodium azide added.

Cyanogen Bromide Cleavage of Peptides for Internal Sequence Analysis

500 μg of SPS enriched protein preparation from the UDPG-agarose stage of the purification schedule is fractionated on a 7.5% Laemmli gel and transblotted onto PVDF membrane. The membrane is then stained for 30 min with Ponceau S (0.5%) in 1% acetic acid. Following destaining in water the band of interest is excised from the membrane and cut into 2–3 mm square fragments which are placed in a Eppendorf tube. 150 μl of 0.5 M CNBr in 70% formate (v:v) is added and the tube incubated in the dark at 25° C. for 16 h with occasional agitation. Excess reagent is removed by evaporation under vacuum. When dry 50 μl of de-ionised water is added, the tube vortexed and the sample re-dried in the vacuum centrifuge. This is repeated a further three times.

After removal of cleavage reagent, 70 μl of elution buffer containing 2% SDS and 1% triton X-100 in 50 mM tris-HCl, pH9.3, is added to the tube containing the sample. The sample is then incubated for 90 min with careful agitation. Glycerol and Bromophenol blue to a final concentration of 6.25% and 0.001% respectively are then added.

The dissolved peptide fragments are then fractionated according to size on a 15% Shagger acrylamide gel and transblotted onto PVDF membrane. The amino acid sequence of the peptides are then determined by Edman degradation (Eur. J. Biochem, 20, 89–102, 1971).

Production of Transgenic Plants with Decreased Suger

An oligonucleotide may be prepared to the amino acid sequence PEEITKE and used to probe a potato tuber cDNA library.

A clone containing the DNA sequence AAGCCGGAG-GAGATTACGAAGGAGGAGTATGCTGCAT-TCTACAAGAGCCTGACAAATGAT TGGGAAGAG-CATTTGGCTGTCAAGCACTTCTCTGTTGAGGGTCA GCTGGAGTTCAAGGCT GTTCTTTTTATTCCAAA-GAGAGCTCCTTTTGACCTCTTTGACAC-CAAGAAGAAGCCCAAC AATATCAAGCTCTATGT-TCGCCGTGTGTTCATCATGGATAACTGCGAGGAATT GATTCCT GAATATTTGAGCTTTGTGAAGGGTAT-TGTGGATTCCGAGGACCTTCCCCTCAACATCTCT AGAGAGATGTTACAGCAGAATAAGATC-CTGAAGGTTATTCGCAAAAACTTGGTAAAGAAG TGCATTGAGCTATTCTTTGAAATCGC-CGAAAACAAAGAAGACTATGACAAGTTCTATGAG GCCTTCTCAAAGAACCTCAAGCTT (referred to as "the operative sequence ie; SEQ ID NO: 1")

Was obtained and blunt end ligated into the plasmid pFW4101 in place of the GUS (β-glucuronidase) coding sequence to give plasmid pFW4131 when the operative sequence is in the sense direction or pFW4132 (drawing herewith) when the operative sequence is in the antisense direction. pFW4101 is constructed with a patatin promoter made from two genomic clones PS3 and PS27. The patatin fragments PS3 and PS27 are derived from the genomic clones described by Mignery et al (Gene 62, 27–44, 1988). The fragments consist of −3.5 kb to −1 kb of PS3 and −1 kb to +3 of PS27 numbered in relation to the translation start.

*E. coli* harbouring pFW4101 was previously deposited, under the Budapest Treaty on the International Recognition of the Deposit of Micro-Organisms for the Purposes of Patent Procedure, at the National Collection of Industrial and Marine Bacteria, Aberdeen, GB on Jul. 5 th 1990 under accession number NCIMB40306.

The vectors pFW4101 (control), pFW4131 (sense) and pFW4132 (antisense) were transferred separately into *Agrobacterium tumefaciens* strain LBA4404 by triparental mating. The Agrobacterium strains were used to transform the potato cultivar Desirée. Those transgenic plants that express the chimaeric gene sufficiently strongly will have a decreased sugar level.

What is claimed is:

1. A method for making a transgenic potato plant comprising:
   (i) transforming a potato cell with a chimeric gene comprising a promoter for expression in a cell of a potato tuber, and the antisense nucleotide sequence of SEQ ID NO: 1; and
   (ii) regenerating a potato plant from the transformed potato cell.

2. The method of claim 1 wherein the promoter is a promoter of the patatin gene.

3. The transgenic potato plant which is the product of the method of claim 1.

4. The transgenic potato plant which is the product of the method of claim 2.

5. A seed of the potato plant of claim 3, wherein the seed comprises the chimeric gene.

6. A seed of the potato plant of claim 4, wherein the seed comprises the chimeric gene.

7. A tuber of the potato plant of claim 3.

8. A tuber of the potato plant of claim 4.

* * * * *